(12) United States Patent
Ingle et al.

(10) Patent No.: US 9,655,668 B2
(45) Date of Patent: May 23, 2017

(54) APPARATUS AND METHOD FOR CHILLING CRYO-ABLATION COOLANT AND RESULTING CRYO-ABLATION SYSTEM

(71) Applicant: BOSTON SCIENTIFIC SCIMED, INC., Maple Grove, MN (US)

(72) Inventors: Frank W. Ingle, Palo Alto, CA (US); Leonard J. George, Scotts Valley, CA (US); Joann Heberer, Portola Valley, CA (US); Raphael Hon, Irvine, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 14/710,288

(22) Filed: May 12, 2015

(65) Prior Publication Data

US 2015/0238243 A1    Aug. 27, 2015

Related U.S. Application Data

(63) Continuation of application No. 12/432,465, filed on Apr. 29, 2009, now Pat. No. 9,028,445.
(Continued)

(51) Int. Cl.
*A61N 1/30* (2006.01)
*A61B 18/02* (2006.01)
(Continued)

(52) U.S. Cl.
CPC .... *A61B 18/02* (2013.01); *A61B 2017/22051* (2013.01); *A61B 2018/0022* (2013.01);
(Continued)

(58) Field of Classification Search
CPC .......... A61B 18/02; A61B 2017/00084; A61B 2017/22051; A61B 2018/0212; A61B 2018/0262
(Continued)

(56) References Cited

U.S. PATENT DOCUMENTS 5,147,355 A    9/1992 Friedman et al.
5,254,116 A    10/1993 Baust et al.
(Continued)

FOREIGN PATENT DOCUMENTS

EP    1129670 A1    9/2001
EP    1158906 B1    12/2001
(Continued)

OTHER PUBLICATIONS

International Preliminary Report on Patentability issued in PCT/US2009/042162, completed Nov. 17, 2010, 6 pages.
(Continued)

*Primary Examiner* — Phillip Gray
(74) *Attorney, Agent, or Firm* — Faegre Baker Daniels LLP

(57) ABSTRACT

Apparatus and methods for cooling liquid coolant, such as nitrous oxide, to be delivered to a cryo-ablation device such as a balloon catheter. A hose or conduit in fluid communication with the ablation device includes an outer member and inner tubes. A first inner tube disposed within a lumen of the outer member carries liquid coolant to the ablation device. Another inner tube also disposed within the lumen carries liquid coolant and terminates within the lumen such that gaseous coolant derived from liquid coolant flowing through the second inner tube flows within the lumen to cool or chill the first inner tube and liquid coolant carried by the first inner tube to the ablation device.

9 Claims, 10 Drawing Sheets

Related U.S. Application Data

(60) Provisional application No. 61/052,598, filed on May 12, 2008.

(51) Int. Cl.
*A61B 17/22* (2006.01)
*A61B 18/00* (2006.01)

(52) U.S. Cl.
CPC ............... *A61B 2018/00166* (2013.01); *A61B 2018/00172* (2013.01); *A61B 2018/00577* (2013.01); *A61B 2018/0212* (2013.01); *A61B 2018/0262* (2013.01)

(58) Field of Classification Search
USPC .................................................. 606/21–22
See application file for complete search history.

(56) References Cited

U.S. PATENT DOCUMENTS

| | | | |
|---|---|---|---|
| 5,674,218 A | 10/1997 | Rubinsky et al. | |
| 5,759,182 A | 6/1998 | Varney et al. | |
| 5,807,391 A | 9/1998 | Wijkamp | |
| 6,027,499 A | 2/2000 | Johnston et al. | |
| 6,106,518 A | 8/2000 | Wittenberger et al. | |
| 6,231,543 B1 | 5/2001 | Hegde et al. | |
| 6,235,019 B1 | 5/2001 | Lehmann et al. | |
| 6,280,439 B1 | 8/2001 | Martin et al. | |
| 6,468,297 B1 | 10/2002 | Williams et al. | |
| 6,576,001 B2 | 6/2003 | Werneth et al. | |
| 6,602,247 B2 | 8/2003 | Lalonde | |
| 6,629,972 B2 | 10/2003 | Lehmann et al. | |
| 6,682,525 B2 | 1/2004 | Lalonde et al. | |
| 6,733,494 B2 | 5/2004 | Abboud et al. | |
| 6,755,823 B2 | 6/2004 | Lalonde | |
| 6,761,714 B2 | 7/2004 | Abboud et al. | |
| 7,022,120 B2 | 4/2006 | Lafontaine | |
| 7,025,762 B2 | 4/2006 | Johnston et al. | |
| 7,081,112 B2 | 7/2006 | Joye et al. | |
| 7,150,745 B2 | 12/2006 | Stern et al. | |
| 7,404,816 B2 | 7/2008 | Abboud et al. | |
| 9,028,445 B2 | 5/2015 | Ingle et al. | |
| 2003/0060762 A1* | 3/2003 | Zvuloni | A61B 18/02 604/113 |
| 2005/0228367 A1 | 10/2005 | Abboud et al. | |
| 2006/0084962 A1 | 4/2006 | Joye et al. | |
| 2006/0122589 A1 | 6/2006 | Abboud et al. | |
| 2007/0161974 A1 | 7/2007 | Abboud et al. | |
| 2007/0167938 A1 | 7/2007 | Zvuloni et al. | |

FOREIGN PATENT DOCUMENTS

| | | |
|---|---|---|
| EP | 2288306 A1 | 3/2011 |
| JP | 07155334 A | 6/1995 |
| JP | 2003503123 A | 1/2003 |
| JP | 2004505664 A | 2/2004 |
| JP | 2005503241 A | 2/2005 |
| JP | 2011521679 A | 7/2011 |
| WO | 0101049 A1 | 1/2001 |
| WO | 0201049 A1 | 1/2002 |
| WO | 0201123 A1 | 1/2002 |
| WO | 0211638 A1 | 2/2002 |
| WO | 03026719 A2 | 4/2003 |
| WO | 2009140066 A1 | 11/2009 |

OTHER PUBLICATIONS

International Search Report and Written Opinion issued in PCT/US2009/042162, mailed Sep. 17, 2009, 13 pages.
Williams, et. al. Alternative Energy Sources for Surgical Atrial Ablation. J. Card. Surg., 19:201-206, 2004.

* cited by examiner

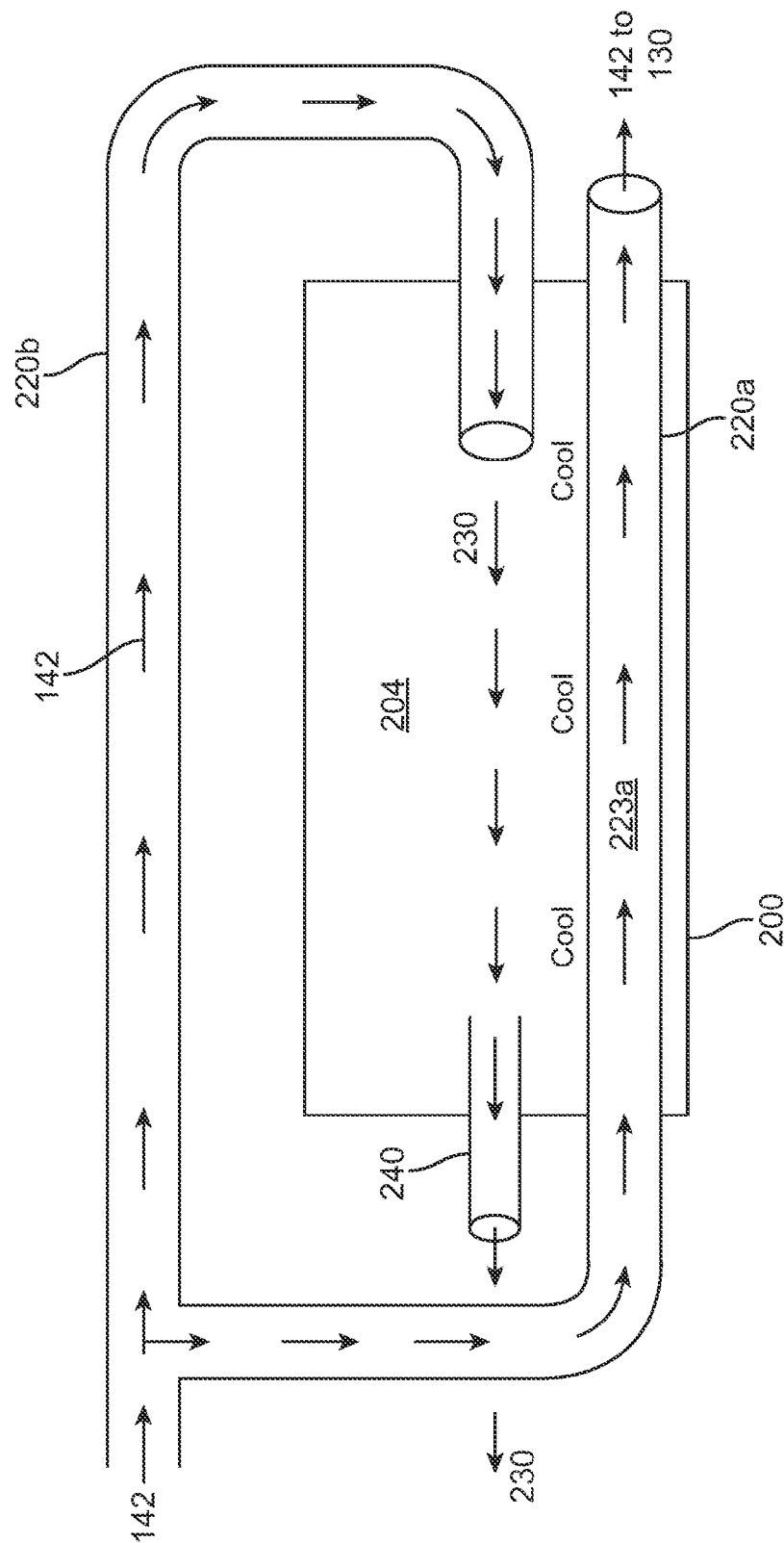

APPARATUS AND METHOD FOR CHILLING CRYO-ABLATION COOLANT AND RESULTING CRYO-ABLATION SYSTEM

CROSS-REFERENCE TO RELATED APPLICATIONS

This application is a continuation of U.S. application Ser. No. 12/432,465, filed on Apr. 29, 2009, now U.S. Pat. No. 9,028,445, which claims priority from the earlier filed U.S. Provisional Application No. 61/052,598, filed May 12, 2008, the entirety of which are hereby incorporated into this application.

FIELD OF THE INVENTION

The present inventions relate to cryo-ablation devices, systems and associated methods.

BACKGROUND

Cardiac arrhythmias are a significant health problem, and atrial fibrillation is a common cardiac arrhythmia. Although atrial arrhythmias may not be as fatal as frequently as ventricular arrhythmias, atrial arrhythmias increase risk factors for other conditions such as embolisms. Further, atrial arrhythmias can contribute to the onset of ventricular arrhythmia.

It is believed that cardiac electrical impulses normally start in a sinoatrial (SA) node, spread through the atria, and progress through the atrial-ventricular (AV) node to the ventricles to complete a heartbeat. Atrial fibrillation is an irregular heart rhythm that originates in abnormal cells in the atria, the upper two chambers of the heart. Muscle fibers in the pulmonary veins, in particular, can be sources of disruptive re-entrant electrical impulses.

One known method of treating atrial fibrillation is by use of medication that is intended to maintain a normal sinus rate and/or decrease ventricular response rates. It is also known to use implant devices such as atrial pacemakers to treat these conditions. Other known methods and devices have been developed for creating therapeutic lesions, e.g., by open-heart or minimally-invasive surgical methods, in the myocardial tissue to block sources of unwanted electrical impulses that are believed to be the source of atrial fibrillation. In this context, ablation has come to mean the deactivation, or removal of function, rather than the removal of the tissue, per se. A number of energy sources may be used for creating these "blocking" lesions that may be transmural and extend across the entire heart wall to isolate the unwanted sources of activation from the rest of the excitable tissue in the heart.

Formation of lesions may be performed using both endocardial and epicardial devices and procedures. Endocardial procedures are performed from within the heart. Since the endocardium primarily controls myocardial functions, there are inherent advantages to generating lesions by applying an energy source to endocardial surfaces. One known manner of applying energy for this purpose is to utilize radio frequency (RF) catheters, which ablate tissue by heating it over about 50° C. Other devices and procedures involve cryo-ablation. Cryo-ablation devices ablate tissue by freezing the tissue to permanently destroy its function. Examples of known lesion formation devices, including cryogenic balloon catheters for use in endocardial ablation and their operation are described in U.S. Patent Application Publication No. 20060084962, U.S. Pat. Nos. 6,027,499; 6,468,297; 7,025,762; 7,081,112 and 7,150,745 and Williams, et al, "Alternative Energy Sources for Surgical Atrial Ablation", J. Card. Surgery, 2004; 19:201-206, the contents of which are incorporated herein by reference as though set forth in full.

The effectiveness of cryogenic balloon catheters depends on various factors including, for example, successfully delivering high quality cryogenic coolant or refrigerant (generally referred to as "coolant") from a pump, pressure reservoir or other refrigerant source and to the target site or tissue to be treated. Certain known cryogenic balloon catheters operate as a closed-loop fluid system. Coolant is fed to the catheter at a high pressure, and cryogenic cooling results from evaporation of the coolant resulting from a pressure drop as the cryogenic fluid is sprayed into the interior of a balloon at the catheter tip. The quality of the coolant, e.g., the relative proportion of the coolant, which may be in liquid state, is determined by the local pressure and temperature of the coolant relative to the vapor saturation line for the coolant. For example, 100% saturation may be preferred.

Ideally, the coolant is delivered to the catheter tip at a sufficiently low temperature and a sufficiently high pressure such that the combination of the low temperature and high pressure is above the vapor saturation line for the coolant. However, during use, the pressure of the liquid coolant drops and the temperature of the coolant may increase as the liquid flows through a coolant supply line or hose and the catheter. The resulting pressure drops and higher temperatures negatively impact the quality of the cryogenic coolant that is delivered to the tip of the cryogenic catheter, increasing fluid resistance, which reduces the rate at which liquid coolant is provided to the catheter tip. This diminishes the cryogenic effect of the coolant and the quality of lesions that are formed thereby. For example, if the temperature of liquid nitrous oxide is increased by a certain degree, gas bubbles will form within the nitrous oxide coolant. These bubbles increase fluid resistance of the coolant as the coolant flows through a small diameter supply tube or conduit, thus reducing the rate at which liquid nitrous oxide coolant can be provided to the tip of the catheter to perform cryo-ablation.

One attempt to address these issues is to maintain the liquid coolant in the supply path adequately above the saturation line by increasing the local pressure, lowering the local temperature, or both. For this purpose, it is known to utilize a cryogenic supply console, which is typically located near the clinician and is used to chill the coolant that is supplied to the catheter. These supply consoles are typically large components and incorporate a compressor or a heat exchanger/chiller to provide coolant at desired pressures and temperatures. For example, one known supply console has a large mechanical compressor that is used to liquefy gas refrigerant at a high pressure, and another known supply console has a heat exchanger/chiller to liquefy the refrigerant vapor and deliver it at a low temperature. Such large supply consoles may initially provide coolant having desired characteristics, but the required console equipment is bulky and of such a size that it is not desirable to have them in operating environments. Other difficulties arise from placing such large consoles at a distance from operating environments due to associated warming of the liquid coolant, increased fluid resistance, and decreased coolant flow to the tip of the catheter.

SUMMARY

According to one embodiment, an apparatus for cooling a coolant to be delivered to a cryo-ablation device includes an outer member having a proximal end and a distal end and defining a lumen, a first inner tube and a second inner tube. The first inner tube is disposed within the lumen and configured to carry coolant to the cryo-ablation device. The second inner tube is disposed within the lumen and configured to carry liquid coolant. A distal end of the second inner tube terminates within the outer member lumen such that gaseous coolant formed by or derived from evaporation of the coolant flowing through the second inner tube flows within the lumen to cool the first inner tube and liquid coolant carried by the first inner tube.

Another alternative embodiment is directed to a cryo-ablation system that includes a cryo-ablation device configured to cryogenically ablate tissue, and a hose or conduit that is in fluid communication with the cryo-ablation device and configured to cool a coolant, such as a liquid coolant, to be delivered to a cryo-ablation device for tissue ablation. The hose or conduit comprises an outer member having a proximal end and a distal end and defining a lumen, a first inner tube and a second inner tube. The first inner tube is disposed within the lumen and configured to carry coolant to the cryo-ablation device. The second inner tube is disposed within the lumen and configured to carry liquid coolant. A distal end of the second inner tube terminates within the outer member lumen such that gaseous coolant formed by or derived from evaporation of the coolant flowing through the second inner tube flows within the lumen to cool the first inner tube and liquid coolant carried by the first inner tube.

Another embodiment is directed to a method of cooling liquid coolant to be delivered to a cryo-ablation device. The method comprises delivering liquid coolant through a first inner tube extending through a lumen defined by an outer member; delivering liquid coolant through a second inner tube positioned within the lumen; and cooling the first inner tube and liquid coolant carried thereby with a gaseous coolant derived from evaporation of liquid coolant released from the second inner tube and into the lumen of the outer member.

In one or more embodiments, the flow of liquid coolant and the flow of gaseous coolant are in different, e.g., opposite, directions.

In one or more embodiments, the outer member may be a heat exchanger sheath. Further, outer members including tubes may include first and second tubes that are substantially parallel to each other such that liquid coolant flows in substantially the same direction in through the first and second inner tubes, whereas gaseous coolant may flow in a second, different direction through the lumen of the outer member to cool the first inner tube and liquid coolant carried thereby. Further, in one or more embodiments, an outer member of a hose may include an outlet or port through which gaseous coolant derived from the liquid coolant may flow out of the outer tube.

In one or more embodiments, an inner tube, such as the second tube, which does not deliver liquid coolant to a cryo-ablation device, may extend through a substantial portion of the outer member, e.g., a distal end of the second inner member may terminated within the outer tube and be adjacent to a distal end of the outer member, whereas an inner tube, such as the first inner tube, that delivers liquid coolant to the cryo-ablation device may extend completely through the outer member.

In one or more embodiments, the hose may include one or more additional inner tubes, e.g., an inner tube coupled to an inter-balloon pressure source or an inner tube to exhaust spent coolant from the cryo-ablation device.

In one or more embodiments, a hose or conduit or outer member may also include or be associated with a temperature sensor located within the outer member and a sensor associated with an inner tube to detect accumulation of liquid coolant within the cryo-ablation device.

In one or more embodiments, gaseous coolant that is used to cool an inner tube that delivers liquid coolant to a cryo-ablation device may be derived from liquid coolant that flows through a different inner tube that does not deliver liquid coolant to the cryo-ablation device.

In one or more embodiments, the liquid coolant may be liquid nitrous oxide, and the gaseous coolant may be gaseous nitrous oxide and other suitable coolants such as gaseous $CO_2$, Argon and $N_2$.

In one or more embodiments, the cryo-ablation device may be a cryogenic catheter, such as a cryogenic balloon catheter.

BRIEF DESCRIPTION OF THE DRAWINGS

Referring now to the drawings in which like reference numbers represent corresponding parts throughout and in which:

FIG. 2B illustrates a supply or extension hose or conduit apparatus constructed according to another embodiment;

DETAILED DESCRIPTION OF ILLUSTRATED EMBODIMENTS

Embodiments relate to systems, apparatus and methods for cooling coolant to be provided to a cryo-ablation device, such as a cryogenic balloon catheter, without the need for large, bulky consoles that are used in known cooling systems, while addressing or improving upon issues of coolant warming, fluid resistance, and reduced coolant flow associated with known systems that use large consoles. Embodiments are able to cool or chill a liquid coolant that is to be provided to a cryo-ablation device at a location that is closer to the operation site and to allow effective cooling at desired locations.

In one or more embodiments, a supply or extension hose or conduit for cooling or chilling liquid coolant that is to be delivered to a cryo-ablation device includes an outer tube, member or sheath and two or more inner conduits or tubes. At least one inner tube within the outer member carries liquid coolant to be delivered to the cryo-ablation device. A different inner tube within the outer member is of a certain length or positioned such that it terminates within the lumen of the outer body and liquid coolant flowing through this inner tube vaporizes into a gaseous coolant, which flows within the outer tube to cool or chill the at least one inner tube and liquid coolant carried thereby that is to be provided to the cryo-ablation device. Thus, embodiments provide "self-chilling" or "self-cooling" supply or extension hoses.

Further, in certain embodiments, gaseous coolant that cools or chills the inner tube and liquid coolant delivered to the ablation device flows in a different direction than liquid coolant. Thus, self-chilling supply or extension hoses may achieve chilling using "counter current" chilling or counter current heat exchange utilizing gaseous coolant that flows in a different direction than liquid coolant. For example, liquid coolant can flow in one direction, e.g., towards the ablation device to which it is to be delivered, and gaseous coolant that cools the liquid coolant may flow within the lumen in an opposite direction to be exhausted at an end of the supply hose that does not interface with the ablation device. This structural configuration provides for chilling of liquid coolant as the liquid coolant flows within an inner tube to the ablation device, while exhausting the gaseous coolant at another end of the supply hose. Further aspects of various embodiments are described with reference to FIGS. 1-7C.

Figure 1:
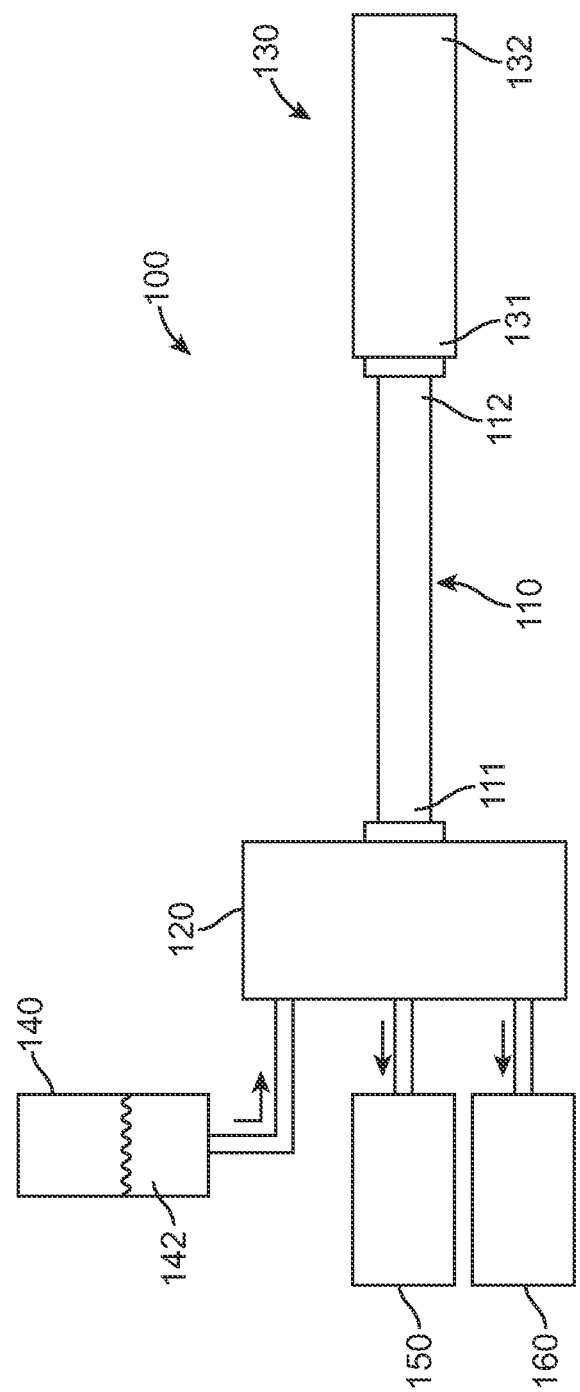
FIG. 1 illustrates a cryo-ablation system constructed in accordance with one embodiment.

Referring to FIG. 1, a cryo-ablation system 100 constructed according to one embodiment includes a self-chilling supply or extension hose or conduit 110 (generally referred to as a supply hose 110), a proximal end 111 of which is associated with, operably coupled to or connected to an interface or small cryogenic console 120 (generally referred to as console 120), and a distal end 112 of which is associated with, operably coupled to or connected to a proximal end 131 of a cryo-ablation device 130. The distal end or tip 132 of the ablation device 130 is used to cryogenically ablate tissue including, but not limited to, cardiac tissue, such as endocardial tissue, using cryogenic fluid 142 that is supplied from a tank or other reservoir 140. An inter-balloon pressure source, pump, tube, lumen or line 150 is provided to control the exhaust pressure of the ablation device 130, and spent cryogenic fluids or materials are evacuated from the ablation device 130 through a catheter exhaust port, tube, lumen or line 160.

According to one embodiment, the cryogenic fluid 142 is a flowable liquid coolant at ambient temperature such as nitrous oxide ($N_2O$), and the system 100 is configured to cryogenically ablate endocardial tissue to treat atrial fibrillation. It should be understood, however, that embodiments may be implemented using other cryogenic refrigerants and fluids 142, and embodiments may be used in various other applications to cryogenically ablate different types of tissue in connection treating other conditions and diseases. For ease of explanation, reference is made to a cryogenic fluid or liquid coolant 142 generally, one example of which is nitrous oxide, which may be used with an ablation device to cryogenically ablate endocardial tissue to treat atrial fibrillation.

Figure 2A:
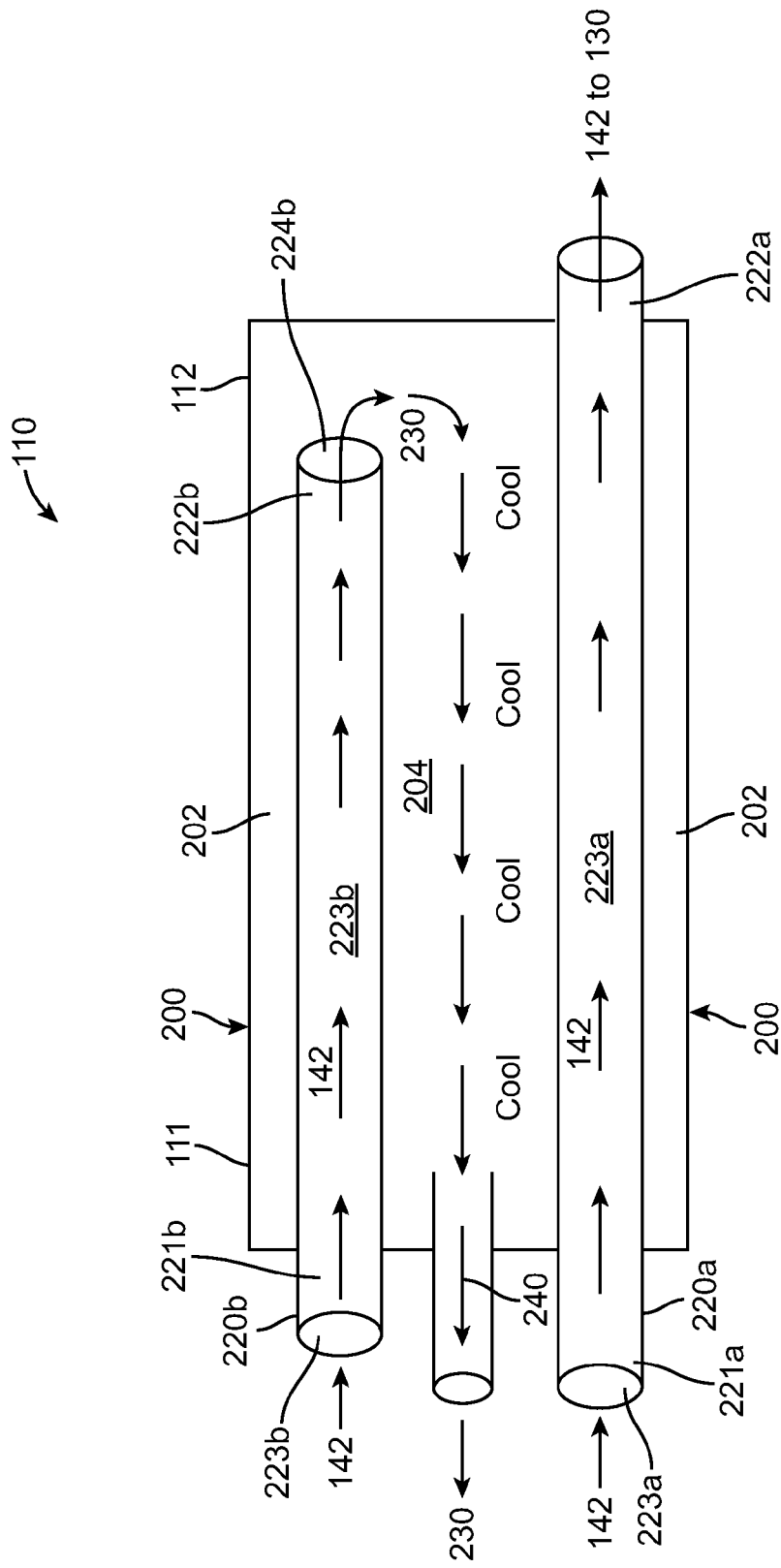
FIG. 2A illustrates a supply or extension hose or conduit apparatus constructed according to one embodiment that may utilize internally generated gaseous coolant and counter flow chilling.

Referring to FIG. 2A, a self-chilling supply or extension hose 110 constructed according to one embodiment includes an outer member or tube 200 that includes or is formed of a sheath 202, e.g., thermally insulative or heat exchanger sheath, which defines an inner space or lumen 204 (generally referred to as lumen 204). The outer member 200 may be made of materials having suitable flexibility, and the heat exchanger sheath 202 may be made of, for example, high pressure reinforced cryogenic tubing. The hose 110 may have a length of about 1 foot to about 10 feet, e.g., about 6 feet and a width of about 0.125" to about 2", e.g., about 0.5". The hose 110 is coupled to the distal end 131 of the cryo-ablation device 130, which may have a length of about 1 foot to about 6 feet, e.g., about 3 feet, and a diameter of about 0.05" to about 0.5", e.g., about 0.1".

With continuing reference to FIG. 2A, in the illustrated embodiment, the outer member 200 includes multiple inner tubes that are disposed or positioned within the lumen 204. In the illustrated embodiment, the supply hose 200 includes first and second inner tubes 220a, 220b, each of which defines respective lumens 223a, 223b through which liquid coolant 142 may flow, and each of which may, for example, be made of a high pressure cryogenic tubing with suitable heat transfer properties. The same source or tank 140 may supply liquid coolant 142 to both of the inner tubes 220a, 220b. Alternatively, different sources or tanks 140 may supply liquid coolant 142 to the inner tubes 220a, 220b. In other embodiments, different coolants 142 flow through the inner tubes 220a, 220b. For ease of explanation, reference is made to a single supply tank 140 that provides coolant 142 to both of the inner tubes 220a, 220b such that the same type of liquid coolant 142 flows through the lumens 223a, 223b of both tubes 220a, 220b, but embodiments are not so limited.

The first inner tube 220a, otherwise referred to as a catheter supply tube, is connected between, or in fluid communication with, the source 140 of liquid coolant 142 and the cryo-ablation device 130. In one embodiment, the first inner tube 220a may have a length of about 1 foot to about 10 feet, e.g., 6 feet, and a width of about 0.01" to about 0.25", e.g., about 0.05". Liquid coolant 142 that flows through the first inner tube 220a is provided to the cryo-ablation device 130 for performing cryogenic endocardial ablation. For example, a proximal end 221a of the first inner tube 220a may be connected to a cryogenic fluid source 140 through the small console 120, and a distal end 222a of the first inner tube 220a may be connected to or interface with a proximal end 131 of the cryo-ablation device 130. An outer surface of the first inner tube 220a may be sealed to the proximal and distal ends 111, 112 of the outer member 200 in a fluid-tight manner.

In the embodiment illustrated in FIG. 2A, the first inner tube 220a extends through the entire length of the supply hose 110 (through the proximal and distal ends 111, 112 of the supply hose 110) such that neither the proximal end 221a nor the distal end 222a of the first inner tube 220a terminates within the supply hose 110, but embodiments are not so limited.

In the embodiment illustrated in FIG. 2A, the second inner tube 220b, otherwise referred to as a chilling coolant supply tube, does not deliver liquid coolant 142 to the cryo-ablation device 130 as does the first inner tube 220a. In one embodiment, the second inner tube 220b may have a length of about 1 foot to about 10 feet, e.g., about 6 feet, and a width of about 0.01" to about 0.25", e.g., about 0.05". In the embodiment illustrated in FIG. 2A, the second inner tube 220b does not extend across the entire length of the supply hose 110. Rather, in the illustrated embodiment, a proximal end 221b of the second inner tube 220b may extend through and be sealed to the proximal end 111 of the outer member 200 in a fluid-tight manner and be in fluid communication with the fluid source 140 and console 120 (similar to the first inner tube 220a described above), but a distal end 222b of the second inner tube 220b terminates within the lumen 204 of the outer member 200. Referring to FIG. 2B, in an alternative embodiment, the second inner tube 220b may be positioned outside of the outer member 200 and be arranged or connected such that the distal end 222b of the second inner tube 220b terminates within the lumen 204 of the outer member 200.

Thus, as generally illustrated in FIGS. 2A-B, the second inner tube 220b may extend through a substantial portion of the outer member 200 (as shown in FIG. 2A) or through small portion of the outer member 200 (as shown in FIG. 2B). Further, FIGS. 2A-B illustrates that coolant 230 released from the second inner tube 220b may flow in different directions within the outer member 200 (as shown in FIG. 2A) or in a single or substantially the same direction (as shown in FIG. 2B).

With these configurations and tube 220a, 220b arrangements, liquid coolant 142 that flows through the lumen 223b of the second inner tube 220b is released through a distal opening 224b of the second inner tube 220b and into the lumen 204 of the outer member 200. The released coolant 142 vaporizes into a gas 230 that flows inside of the outer member 200. The resulting gas 230 cools the first inner tube 220a and the liquid coolant 142 carried thereby. For example, the temperature of the high pressure liquid coolant may be cooled to near the temperature of the saturation line at ambient temperature. For nitrous oxide, this is about −80° C. Although these different embodiments may be utilized and function in similar manners, reference is made to the apparatus configuration shown in FIG. 2A for ease of explanation.

More particularly, FIG. 2A generally illustrates gaseous coolant 230 flowing along one side of the first inner tube 220a, or along the top of the first inner tube 220a in the embodiment illustrated in FIG. 2A. However, during use, gaseous coolant 230 may flow along or over various other sides or surfaces of the first inner tube 220a, e.g., around the entire first inner tube 220a. Thus, FIG. 2A is provided to generally illustrate flow of gaseous coolant 230 along the first inner tube 220a. The second inner tube 221a may have a spirally wrapped filament, tube or other suitable structure (not shown in FIGS. 2A-B), which allows the gaseous coolant 230 to pass or flow next to the first inner tube 221a while preventing the first inner tube 221a from touching the inner surface of the outer member 200, thus enhancing chilling effects and insulation.

These counter current chilling or heat exchange configurations allow liquid coolant 142 to be chilled or cooled within the supply hose 110 using internally generated gaseous coolant 230, thus providing a self-chilled supply hose 110. The chilled liquid coolant 142 that flows through the first inner tube 220a may then be delivered to the cryo-ablation device 130 at desired temperatures and pressures as a result of being chilled by the internally generated gaseous coolant 230. For this purpose, it still may be necessary to use some type of console 120, but not the large, bulky consoles of known systems. Further, with embodiments, it is not necessary for the console 120 to include an independent chiller, compressor or pressurizing apparatus as in known, larger consoles. Thus, with embodiments, additional liquid coolant 142 is utilized for self-chilling in order to reduce the footprint and components of the console 120 such that significantly smaller consoles 120, e.g., portable and disposable consoles 120 that do not include chillers, may be utilized instead, while also achieving lower coolant 142 temperatures at the cryo-ablation device 130 for more effective cryo-ablation of tissue.

In embodiment illustrated in FIG. 2A, self-chilling of the inner tube 220a and coolant 142 carried thereby is achieved utilizing counter current flows. More specifically, liquid coolant 142 flows in substantially the same direction through the first and second inner tubes 220a, 220b, but gaseous coolant 230 flows within the outer member 200 in a different direction to cool the first inner tube 220a and liquid coolant 142 provided to the cryo-ablation device 130. In the illustrated embodiment, the first and second inner tubes 220a, 220b are substantially parallel to each other (although they may be configured in different manners), and liquid coolant 142 flows in a first direction towards the distal end 112 of the supply tube 110 and the ablation device 130, whereas in the illustrated embodiment, gaseous coolant 230 flows in an opposite direction towards the proximal end 111 of the supply tube 110 and is released through an exhaust port or tube 240. Other embodiments may involve flow of liquid coolant 142 and gaseous coolant 230 that are in different directions, but not necessarily opposite directions. Further, in the embodiment illustrated in FIG. 2A, the exhaust port or tube 240 is defined or extends through the proximal end 111 of the outer member 110, but other embodiments may utilize an exhaust port 240 that is defined through a different section of the outer member 200 depending on, for example, the number and orientation of inner tubes 220 within the outer member 200.

Further, the degree of self-cooling utilizing counter current heat exchange or chilling can be adjusted by configuring the tubes 220a, 220b in different positions or configurations, e.g., as shown in FIGS. 2A-B. As a further example, in the illustrated embodiment, the distal end 222b of the second inner tube 220b is close to or adjacent to the distal end or wall 112 of the outer member 200 such that gaseous coolant 230 released by the second inner tube 220b flows through a substantial portion of the outer tube lumen 204 and comes into contact with a substantial portion of the outer surface of the first inner tube 220a. If more cooling is desired, the second inner tube 220b may be positioned closer to the distal end 112 of the outer tube 110, closer to the first inner tube 220a. Further, larger quantities of liquid coolant 142 may be provided through the second inner tube 220b in order to generate larger quantities of gaseous coolant 230 to enhance chilling. Moreover, the surface area of the first inner tube 220a that is exposed to or in thermal contact with the gaseous coolant 230 may be increased. Additionally, the time during which the first inner tube 220 is exposed to or in thermal contact with the gaseous coolant 230 may be increased. Thus, embodiments can be adapted to satisfy different self-chilling or internal cooling needs and different system and ablation device 130 configurations.

Figure 3:
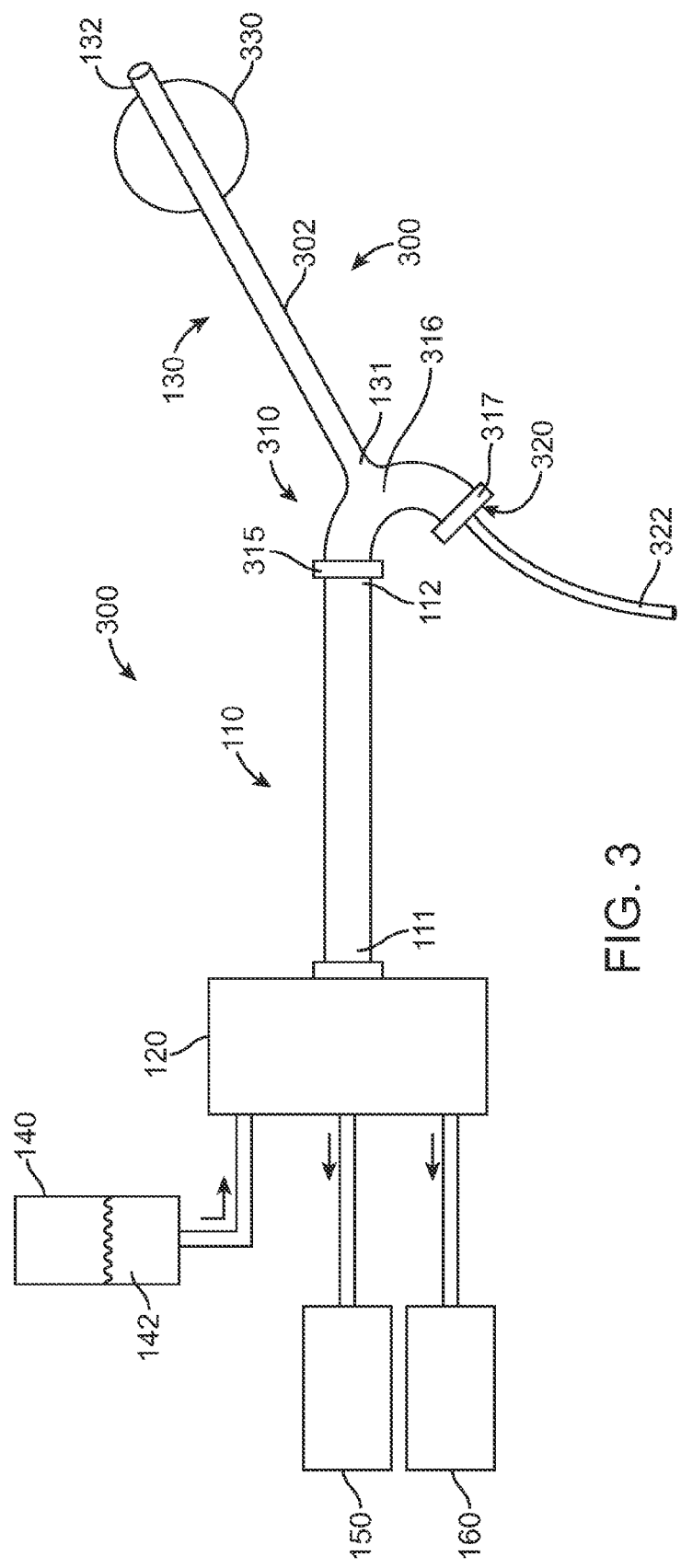
FIG. 3 illustrates a cryo-ablation system constructed in accordance with one embodiment that includes a cryogenic balloon catheter.

Referring to FIG. 3, a system 300 constructed according to another embodiment includes a self-chilling supply hose 110 (e.g., as described with reference to FIGS. 1-2) and a cryo-ablation device 130 in the form of a cryogenic balloon catheter 300 that is coupled to or in fluid communication with the supply hose 110 via an interface 310. In the illustrated embodiment, the cryogenic balloon catheter 300 includes a dilation-type cryogenic balloon tip that includes a balloon member 330. Further, in the illustrated embodiment, the interface 310 is in the form of a Y-adapter. A first portion 315 of the Y-adapter is coupled to the distal end 112 of the supply hose 110, a second portion 316 of the Y-adapter is coupled to a proximal end 131 of the cryo-ablation device 130. In a third portion 317 of the Y-adapter, a guide wire lumen 320 accommodates a guidewire 322 that may include a steerable or deflectable tip for facilitating insertion and positioning of the cryogenic balloon catheter 300 within a patient.

Figure 4:
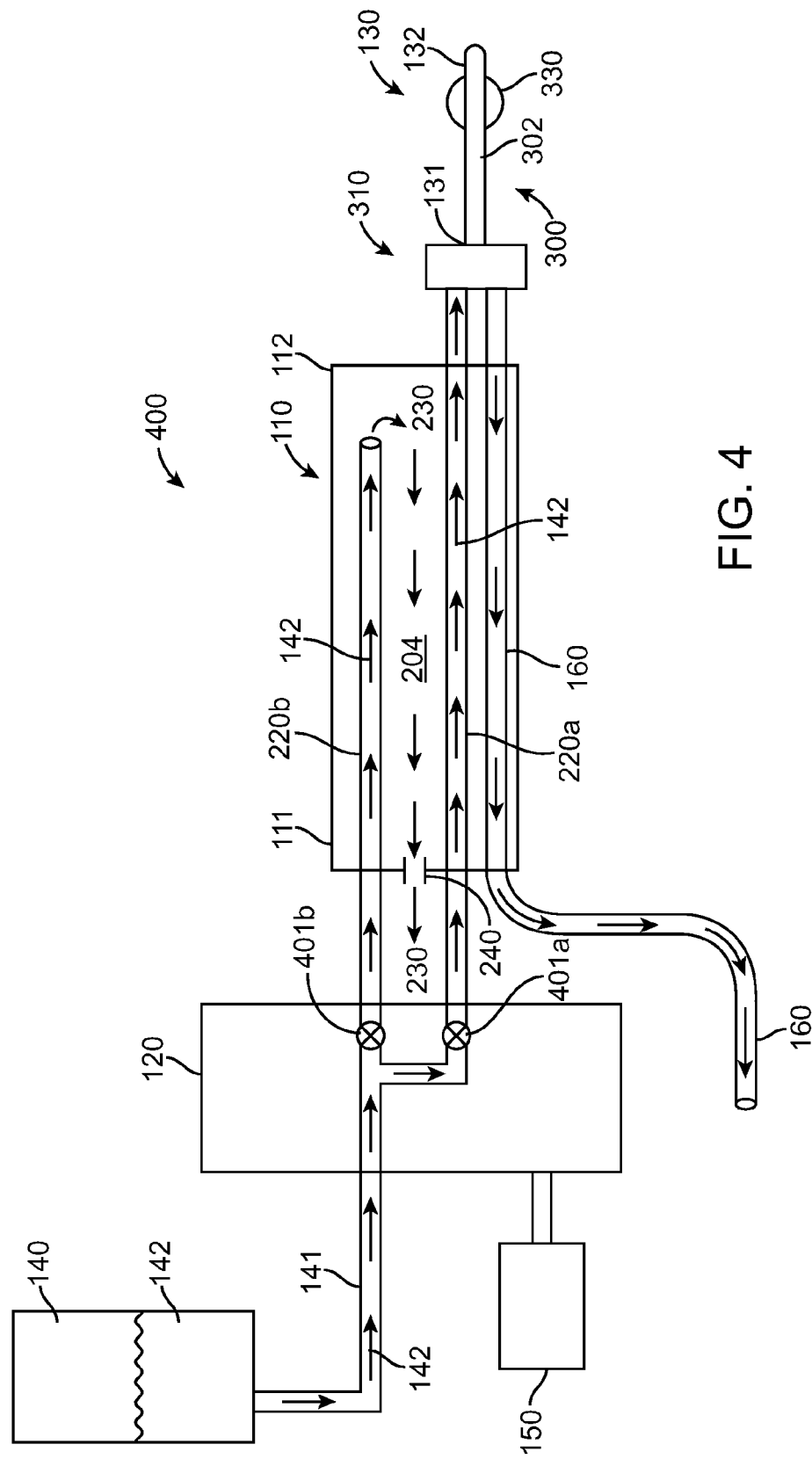
FIG. 4 illustrates an embodiment of a cryo-ablation system in which a catheter exhaust tube or lumen extends through the supply or extension hose shown in FIG. 2A.

With further reference to FIG. 4 (which omits the guide lumen 320 and wire 322 for ease of illustration), the console 120 may include one or more valves 401a, 401b (generally 401) that may be utilized to control the delivery of liquid coolant 142 from the supply tank 140 to the inner tubes 220a, 220b of the supply tube 110. In the illustrated embodiment, the first inner tube 220a may be cooled by gaseous coolant 230 by opening the valve 401b so that liquid coolant 142 flows through the lumen 223b of the second inner tube 220b, and the valve 401a may be opened to allow the liquid coolant 142 chilled by the gaseous coolant 230 to flow through the lumen 223a of the first inner tube 220a and be delivered to the cryogenic balloon catheter 300. Although FIG. 4 shows two valves 401a, 401b and a supply line 141 that is split into the first and second inner tubes 220a, 220b configuration, other valve and supply line configurations may also be utilized to provide a liquid coolant 142 to the supply hose 110.

Figure 5:
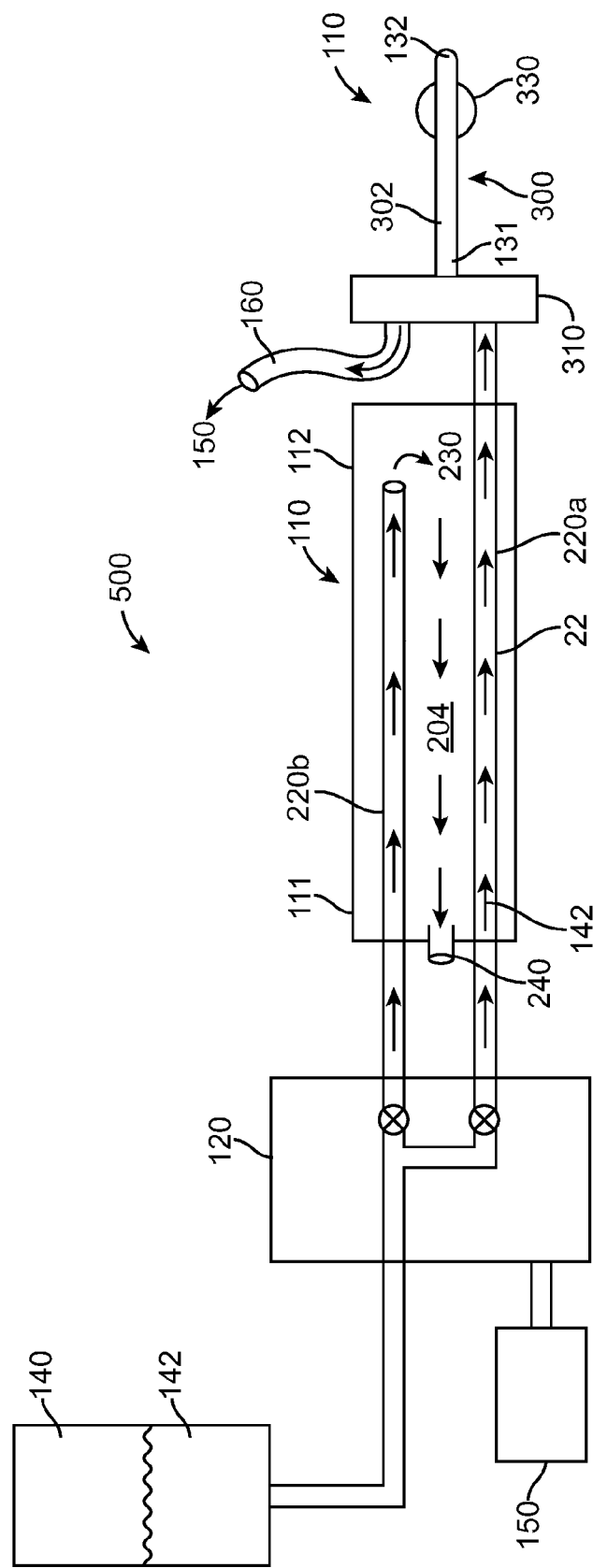
FIG. 5 illustrates another embodiment of a cryo-ablation system in which a catheter exhaust tube or lumen does not extend through the supply or extension hose shown in FIG. 2A.
Figure 6A:
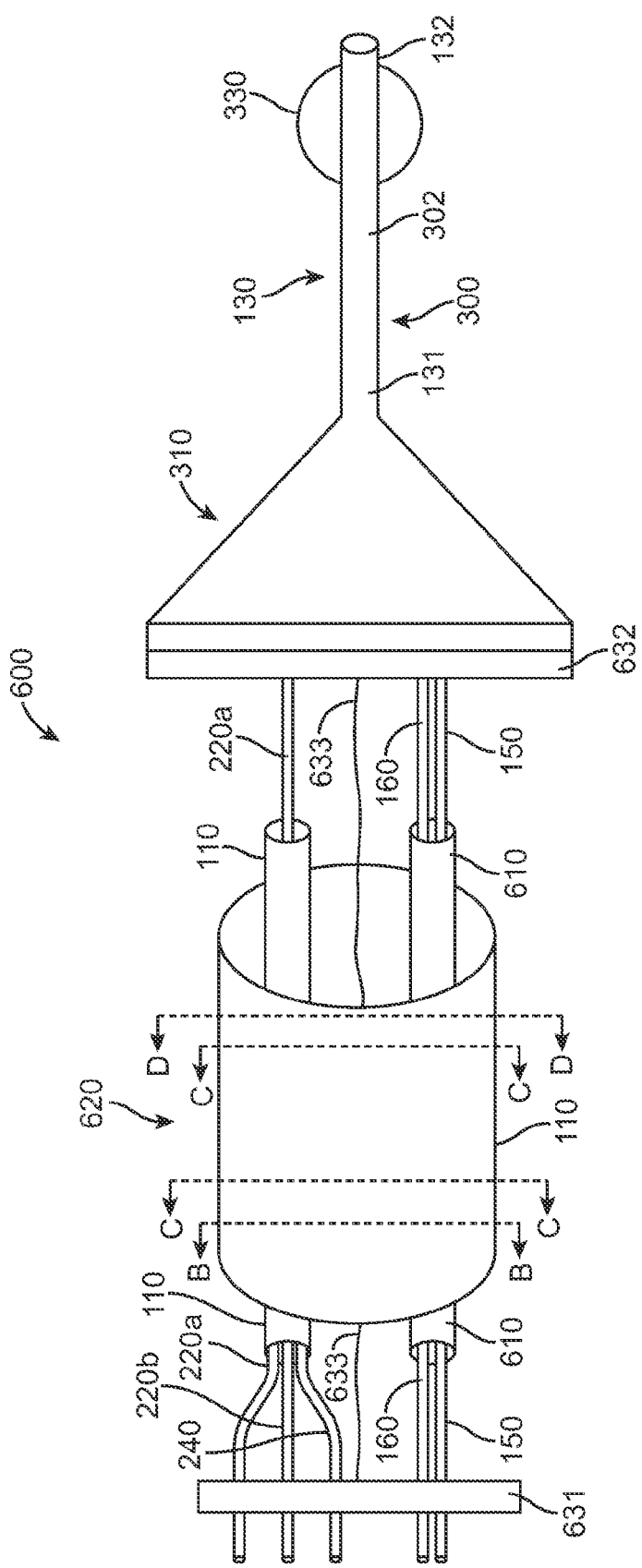
FIG. 6A illustrates a cryo-ablation system constructed according to another embodiment.
Figure 6D:
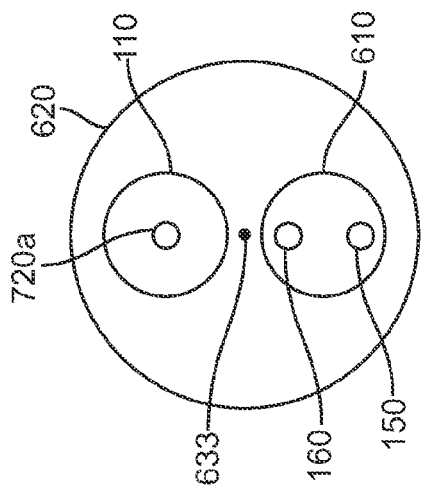
FIG. 6D is a cross-sectional view of FIG. 6A along line D-D.
Figure 6C:
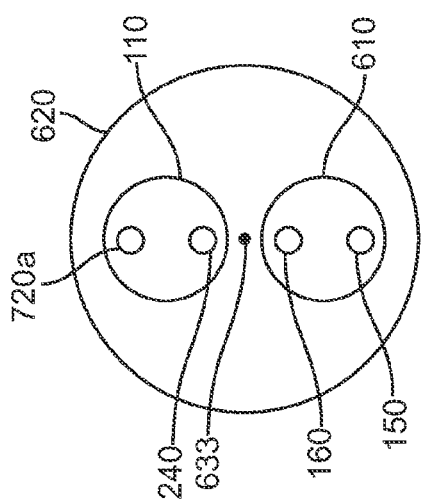
FIG. 6C is a cross-sectional view of FIG. 6A along lines C-C.
Figure 6B:
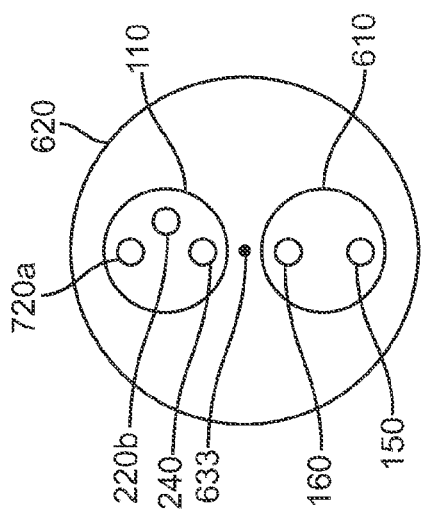
FIG. 6B is a cross-sectional view of FIG. 6A along line B-B.

Referring again to FIG. 3, in one embodiment, the exhaust tube or lumen 160 for evacuating spent coolant from the cryogenic balloon catheter extends through the supply tube 110 and the console 120. In another embodiment, as shown in FIG. 4, the exhaust tube or lumen 160 extends through the supply tube 110, but not the console 120. In a further embodiment, as shown in FIG. 5 (in which a guidewire lumen 320 and guidewire 322 are also omitted for clarity), the exhaust tube or lumen 160 may extend from the interface 310, but not through the supply tube 110 or the console 120. Thus, FIGS. 3-5 show that spent coolant can be evacuated from the cryo-ablation catheter 300 in different ways and may extend through different system components. FIGS. 6A-7C illustrate further embodiments of systems that include a self-chilling supply hose 110 that utilizes internally generated gaseous coolant 230 that may flow through the supply hose 110 in a different direction than liquid coolant 142 to cool or chill liquid coolant 142 before it is provided to a cryo-ablation catheter 300.

Referring to FIGS. 6A-D, a system 600 constructed according to another embodiment includes a self-chilling supply or extension hose 110 and an inner sheath 610 disposed within a larger, outer sheath 620. In the illustrated embodiment, inter-balloon pressure and catheter exhaust tubes or lines 150, 160 are enclosed within a sheath 610 that extends through an outer sheath 620 that encloses the sheath 610 and the supply tube 110. The first inner tube 220a (the catheter supply tube), the second inner tube 220b (chilling coolant supply tube), the exhaust port or tube 240 to exhaust gaseous coolant 230, the inter-balloon pressure tube 150 and catheter exhaust tube 160 may be connected to a proximal connector 631 to facilitate connection to or interfacing with the console 120 or another system component. One suitable proximal connector 631 that may be used with embodiments is a latching connector. Similarly, a distal hose connector 632 is adapted to connect the first inner tube 220a (the catheter supply tube), the inter-balloon pressure tube 150 and the catheter exhaust tube 160 to the interface 310 such that these tubes are in fluid communication with the cryogenic balloon catheter 300. Latching connectors may also be used for this purpose. The proximal and distal hose connectors 631, 632 may also be advantageously connected by a strain relief wire 633 to protect the connectors 631, 632 from damage of disconnection if inadvertently pulled. During use, the first inner tube 220a is cooled by gaseous coolant 230 derived from liquid coolant 142 flowing through the second inner tube 220b, and chilled liquid coolant 142 is provided by the first inner tube 220a to the cryogenic balloon catheter. As a result, the balloon member 330 expands, and cardiac tissue adjacent to the balloon member 330 may be cryogenically ablated. Spent coolant is evacuated from the cryogenic balloon catheter 300 through the exhaust port or tube 240.

Figure 7A:
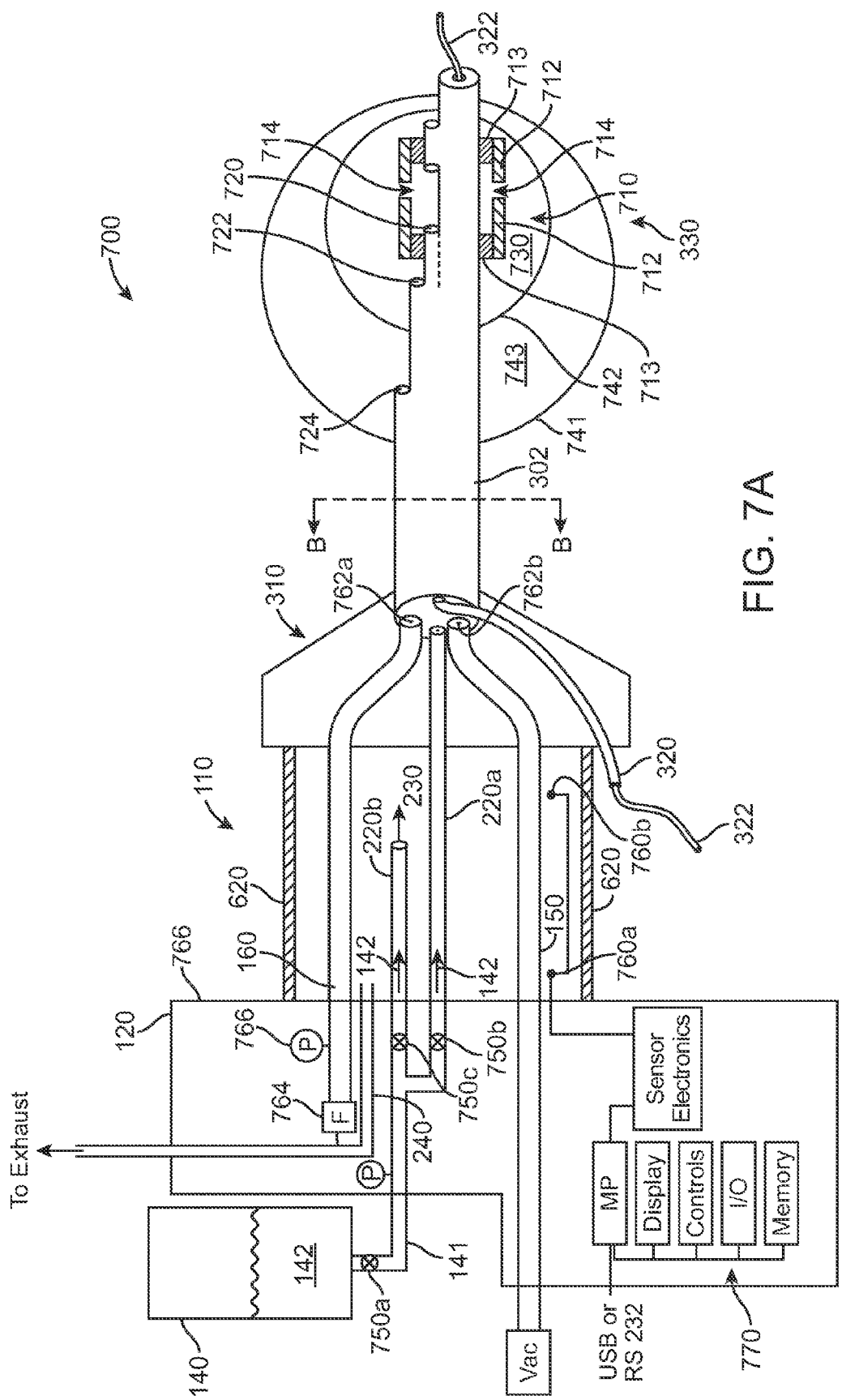
FIG. 7A schematically illustrates a cryo-ablation system constructed according to a further alternative embodiment.
Figure 7C:
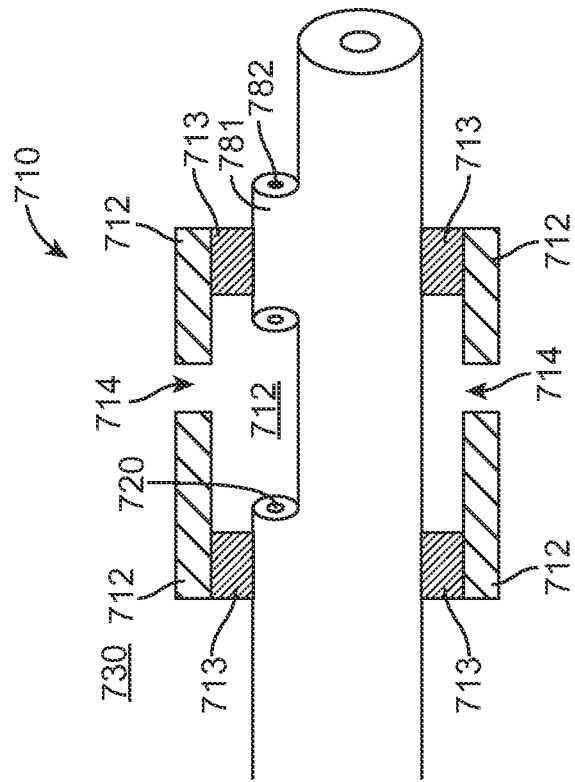
FIG. 7C is an enlarged view of a dispersion manifold shown in FIG. 7A.
Figure 7B:
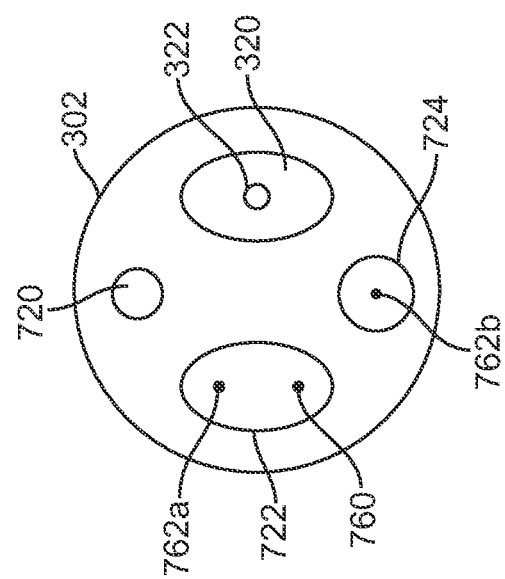
FIG. 7B is a cross-section view of FIG. 7A along line B-B.

FIGS. 7A-C illustrate another system 700 that includes a self-chilling supply or extension hose 110 and how other system components can be operably connected to perform cryo-ablation. In the illustrated embodiment, the first inner tube 220a may extend into the catheter 300, or be connected to or in fluid communication with a separate catheter supply tube or lumen 720 that extends through the body 302 of the cryogenic balloon catheter 300, such that at least one tube or lumen, whether the first inner tube 220a or the internal catheter supply tube or lumen 720, supplies previously chilled liquid coolant 142.

In the illustrated embodiment, a distal end of the elongate body 302 or extrusion, includes a dispersion member or manifold 710, which is used to distribute coolant. The dispersion member 710 extends from the elongate body 302 and defines an internal lumen or space 712 that is in fluid communication with a distal end or outlet of the catheter supply tube 720. In the illustrated embodiment, the dispersion member 710 includes dispersion elements 712 that are sealingly engaged or connected, e.g., welded 713, to the elongate body 302 to define nozzles or apertures 714 through which coolant is distributed. The outlet 782 of tubular element 781 is blocked or sealed. For example, during assembly of the manifold 710, the seals can be welded 713, and a gas may be blown through tubular element 781 to clear out particles, and then the tubular element 781 may be sealed 782. This prevents or reduces particles blocking nozzles 714.

In the illustrated embodiment, the balloon 330 includes an outer wall 741 that surrounds or encloses an inner wall 742 to define an intermediate space 743 between the balloon outer and inner walls 741, 742. The balloon 330 also defines an internal chamber 730 defined by an inner surface of the inner wall 742. The outlet of the supply tube or lumen 720 through which pre-chilled liquid coolant 142 flows is in fluid communication with the internal space 712 of the dispersion member 710 and the internal chamber 730. The catheter exhaust tube or lumen 160, or another tube or lumen 722 that extends through the elongate body 302, is in fluid communication with the internal chamber 730. The inter-balloon pressure tube or lumen 150, or a separate tube or lumen 724 that extends through the body 302, is in fluid communication with the intermediate space 743 defined between the walls 741, 742 of the balloon 370.

During use, liquid coolant 142 is provided to the supply hose 110 from the supply tank 140 by opening one or more valves 750a-c. The liquid coolant 142 may flow through a supply line 141, which may divided or split into two separate inner lines or tubes 220a, 220b (as shown in FIG. 4). In the illustrated embodiment, liquid coolant 142 flowing through the first inner tube 220 at is chilled by counter-flowing gaseous coolant 230. One or more temperature sensors or thermocouples 760a, 760b (generally referred to as temperature sensor 760) may be utilized to monitor the effect of chilling of the liquid coolant 142 within the supply hose 110, e.g., by use of a controller, microprocessor, or other suitable hardware and software, generally identified as 770 in FIG. 7A. Chilled liquid coolant 142 flows through the first inner tube 220a and the catheter supply tube or lumen 720a and is released into the internal space 712 of the dispersion member 710.

Due to the resulting pressure drop resulting from chilled liquid coolant 142 being released into the space 712, the chilled liquid coolant 142 is chilled into a spray of very cold liquid and gas. The pressure of the liquid coolant 142 and supply line 720 dimensions are such that the very cold, partially liquid coolant 142 sprays against an inner surface of the inner balloon wall 742, absorbs heat, and evaporates rapidly, thereby causing the expandable balloon 742 to inflate. During ablation, the walls of the balloons 741, 742 are pressed together and press on the tissue to be ablated. Cryo-ablation is accomplished by the resulting rapid cooling of the balloon walls 741, 742 while the outer balloon wall 741 is positioned against or within cardiac tissue that is being ablated.

Spent gaseous coolant is then evacuated through the tube or lumen 722 and the outlet port or tube 150. The flow and pressure of the spent gaseous coolant exhausted from the catheter 300 may be monitored with a coolant flow sensor 764, a pressure sensor 766 or other suitable devices. Further, one or more flood sensors 762a, 762b may be positioned within the catheter exhaust lumen 160 and/or the inter-balloon pressure lumen 150 to monitor the presence of electrically conductive liquids (e.g., blood) within the catheter 300 in order to determine whether the inter-balloon pressure level should be adjusted or the coolant flow should be stopped, e.g., using the controller 770 or other suitable components.

Although particular embodiments have been shown and described, it should be understood that the above discussion is not intended to limit the scope of these embodiments. Various changes and modifications may be made without departing from the scope of the claims. For example, embodiments may be configured to perform ablation of various types of tissue for treatment of different conditions or diseases, one example of which is to perform endocardial ablation to treat atrial fibrillation as described above. Other embodiments may be implemented to cool or chill liquid coolants provided to cryo-ablation devices that are components of open-loop, or closed-loop, fluid-fed catheter systems.

Moreover, although embodiments are described herein with reference to a self-chilling supply hose that utilizes internally generated gaseous nitrous oxide to cool or chill liquid nitrous oxide, in other embodiments, gaseous nitrous oxide may be used to chill or cool different types of liquid coolants and refrigerants, and that the gaseous coolant may be a gaseous coolant other than gaseous nitrous oxide. Further, coolants as described herein may, in certain embodiments, and depending on the coolant used, be a flowable mixture of a gas and a liquid. Thus, although a coolant may be a "liquid" or have liquid-like properties, the coolant may be a flowable or fluid mixture of a liquid and a small amount of gas. Further, the coolant carried by the second inner tube that is utilized to cool or chill coolant that is carried by the first inner tube and to the cryo-ablation device may be the same type of coolant or different types of coolants, and may be the same phase (e.g., a liquid) or different phases.

Embodiments may also be implemented utilizing a supply hose individually (which may be disposable), or as a combination of a supply hose and catheter (the combination of which may also be disposable), and as combinations of other system components described above.

Thus, embodiments are intended to cover alternatives, modifications, and equivalents that may fall within the scope of the claims.

What is claimed is:

1. A method of supplying cooled liquid coolant to a cryo-ablation device, comprising:
   delivering liquid coolant through a first inner tube extending through a lumen defined by an outer member coupled to the ablation device, the first inner tube in fluid communication with an interior of the ablation device;
   delivering liquid coolant through a second inner tube at least partially positioned within the outer member lumen; and
   cooling the first inner tube and liquid coolant carried therein with a gaseous coolant derived from evaporation of liquid coolant released from the second inner tube and into the outer member lumen.

2. The method of claim 1, the first and second inner tubes being configured and arranged such that liquid coolant flows through the first inner tube in a first direction, and gaseous coolant flows in the outer member lumen in a second direction different than the first direction.

3. The method of claim 2, wherein the first direction and the second direction are opposite directions.

4. The method of claim 1, further comprising exhausting the gaseous coolant through an outlet defined by the outer member lumen.

5. The method of claim 1, wherein the first inner tube is not in fluid communication with the second inner tube or the outer member lumen.

6. The method of claim 1, further comprising monitoring an effect of the cooling the first inner tube and liquid coolant carried therein by monitoring a temperature of the first inner tube and liquid coolant carried therein within the outer member lumen.

7. The method of claim 1, further comprising exhausting spent coolant from the ablation device through a third tube extending through the outer member lumen.

8. The method of claim 7, further comprising monitoring a pressure of the spent coolant exhausting from the ablation device.

9. The method of claim 7, further comprising monitoring a flow rate of the spent coolant exhausting from the ablation device.

* * * * *